(12) United States Patent
Grossmann et al.

(10) Patent No.: US 9,487,576 B2
(45) Date of Patent: Nov. 8, 2016

(54) METHOD FOR REDUCTION OF 1->2 READING FRAME SHIFTS

(71) Applicant: Hoffmann-La Roche Inc., Little Falls, NJ (US)

(72) Inventors: Adelbert Grossmann, Eglfing (DE); Friederike Hesse, Munich (DE); Erhard Kopetzki, Penzberg (DE); Wilma Lau, Munich (DE); Christian Schantz, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/473,017

(22) Filed: Aug. 29, 2014

(65) Prior Publication Data

US 2015/0056656 A1 Feb. 26, 2015

Related U.S. Application Data

(63) Continuation of application No. PCT/EP2013/053547, filed on Feb. 22, 2013.

(30) Foreign Application Priority Data

Feb. 29, 2012 (EP) .................................. 12157512.0
Apr. 2, 2012 (EP) .................................. 12162810.1

(51) Int. Cl.
*C07K 14/775* (2006.01)
*C12N 15/67* (2006.01)

(52) U.S. Cl.
CPC ............. *C07K 14/775* (2013.01); *C12N 15/67* (2013.01)

(58) Field of Classification Search
CPC  C12N 2799/021; C12N 15/70; C12N 15/52; A61K 38/00
See application file for complete search history.

(56) References Cited

U.S. PATENT DOCUMENTS

| 5,202,238 A | 4/1993 | Fell, Jr. et al. |
| 5,204,244 A | 4/1993 | Fell et al. |
| 6,291,245 B1 | 9/2001 | Kopetzki et al. |

FOREIGN PATENT DOCUMENTS

| EP | 0 972 838 B1 | 7/1999 |
| EP | 1 486 571 B1 | 6/2003 |
| WO | 95/25786 A1 | 9/1995 |
| WO | 2011/143362 A1 | 11/2011 |

OTHER PUBLICATIONS

Huang et al. Selection for minimization of translational frameshifting errors as a factor in the evolution of codon usage. Nucleic Acids Research, 2009, vol. 37, No. 20 6799-6810.*
Ausubel et al. Current Protocols in Molecular Biology United States: John Wiley and Sons, Inc., vol. vols. I to III (1997).
Beck et al., "Nucleotide Sequence and Genome Organisation of Filamentous Bacteriophages f1 and fd" Gene 16:35-58 (1981).
Bujard et al., "A T5 Promoter-Bases Transcription-Translation System for the Analysis of Proteins in Vitro and In Vivo" Methods in Enzymology 155:416-433 ( 1987).
Farabaugh, P.J., "Sequence of lacI Gene" Nature 274(24):765-769 ( 1978).
Graversen et al., "Trimerization of Apolipoprotein A-I retards Plasma Clearance and Preserves Anthiatherosclerotic Properties" Journal Cardiovasc Pharmacol. 51:170-177 (2008).
Green et al., "Characterization of the Mechanical Unfolding of RNA Pseudoknots" Journal of Molecular and Biology 375:511-528 ( 2008).
Gurvich et al., "Sequences that Direct Significant Levels of Frameshifting are Frequent in Coding Regions of *Escherichia coli*" The EMBO Journal 22(21):5941-5950 ( 2003).
International Search Report for PCT/EP2013/053547, mailed dated May 8, 2013, pp. 5.
J Chromatography Library "Chromatography" Heftmann, E. Elsevier Scientific Publishing Company, ( 1983).
Karathanasis et al., "Isolation and Characterization of the Human Apolipoprotein A-I Gene" Proc. Natl. Acad. Sci. USA 80:6147-6151 ( 1983).
Laemmli et al., "Cleavage of Structural Proteins During the Assembly of the Head of Bacteriophage T4" Nature 227:680-685 ( 1970).
Morrison et al., "Chimeric Human Antibody Molecules: Mouse Antigen-Binding Domains with Human Constant Region Domains" P.N.A.S. USA 81:6851-6855 ( 1984).
Poole et al., "Chromatography Today" Elsevier Science ( 1991).
Queen et al., "A humanized Antibody that Binds to the Interleukin 2 Receptor" P.N.A.S. USA 86:10029-10033 ( 1989).
Riechmann et al., "Reshaping Human antibodies for Therapy" Nature 332:323-327 ( 1988).
Rose et al., "Structure and Function of the Yeast URA3 Gene: Expression in *Escherichia coli*" Gene 29:113-124 ( 1984).
Sambrook et al. Molecular Cloning 2nd Edition,Cold Spring Harbor Laboratory Press, ( 1989).
Schwarz et al., "Nucleotide Sequence of cro, cII and Part of the O Gene in Phage 7 DNA" Nature 272:410-414 ( 1978).
Stueber et al., "System for high-Level Production in *Escherichia coli* and Rapid Purification of Recombinant Proteins: Application to Epitope Mapping, Preparation of Antibodies, and Structure-Function Analysis" Immunological Methods IV:121-152 ( 1990).
Sutcliffe et al., "Complete Nucleotide Sequence of the *Esherichia coli* Plasmid pBR322" The Biological Laboratories 43:77-90 ( 1979).
Graversen et al., "Trimerization of apolipoprotein A-I retards plasma clearance and preserves antiatherosclerotic properties" J Cardiovasc Pharmacol. 51(2):170-176 ( 2008).

(Continued)

*Primary Examiner* — Kagnew H Gebreyesus
(74) *Attorney, Agent, or Firm* — Genentech, Inc.

(57) ABSTRACT

Herein is reported a method for the recombinant production of a polypeptide, which comprises the dipeptide AR, characterized in that the method comprises the recovering of the polypeptide from the cells or the cultivation medium of a cultivation of a cell comprising a nucleic acid encoding the polypeptide and thereby producing the polypeptide, whereby the dipeptide AR comprised in the polypeptide is encoded by the oligonucleotide gca cgt, or the oligonucleotide gcg cgt, or the oligonucleotide gcc cgt.

3 Claims, 1 Drawing Sheet

(56) References Cited

OTHER PUBLICATIONS

Green et al., "Characterization of the Mechanical Unfolding of RNA Pseudoknots" Journal of Molecular and Biology 375:511-528 (2008).

Gurvich et al., "Sequences that Direct Significant Levels of Frameshifting are Frequent in Coding Regions of *Escherichia coli*" The EMBO Journal 22(21):5941-5950 (2003).

Huang, Y. et al., "Selection for minimization of translational frameshifting errors as a factor in the evolution of codon usage" Nucleic Acids Research 37(20):6799-6810 (2009).

Karathanasis et al., "Isolation and Characterization of the Human Apolipoprotein A-I Gene" Pro. Natl. Acad. Sci. USA 80(20):6147-6151 (1983).

* cited by examiner 744 agaaaacggtggtgtgcgaggctagcggaataccacgcaaaa 783
    E  N  G  G  A  R  L  A 1 base (a760) deleted or skipped during transcription or translation 744 agaaaacggtggtgtgcggagctag 765
    E  N  G  G  A  G  stop

SEQUENCE LISTING

```
<160> NUMBER OF SEQ ID NOS: 63

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 gcgagg                                                                    6

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 gcgaga                                                                    6

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 gcacgt                                                                    6

<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4 gcgcgt                                                                6

<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 gcccgt                                                                6

<210> SEQ ID NO 6
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Arg
1

<210> SEQ ID NO 7
<211> LENGTH: 267
<212> TYPE: PRT
<213> ORGANISM: Homo sapiens

<400> SEQUENCE: 7
```

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu

```
              210                 215                 220
Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 8
<211> LENGTH: 5
<212> TYPE: PRT
<213> ORGANISM: Homo sapiens

<400> SEQUENCE: 8

Ser Leu Lys Gly Ser
1               5

<210> SEQ ID NO 9
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Tetranectin-apolipoprotein A-I fusion
      polypeptide comprising expression and purification tags

<400> SEQUENCE: 9

Cys Asp Leu Pro Gln Thr His Ser Leu Gly Ser His His His His
1               5                   10                  15

His Gly Ser Val Val Ala Pro Pro Ala Pro Ile Val Asn Ala Lys Lys
                20                  25                  30

Asp Val Val Asn Thr Lys Met Phe Glu Glu Leu Lys Ser Arg Leu Asp
            35                  40                  45

Thr Leu Ala Gln Glu Val Ala Leu Leu Lys Glu Gln Gln Ala Leu Gln
    50                  55                  60

Thr Val Asp Glu Pro Pro Gln Ser Pro Trp Asp Arg Val Lys Asp Leu
65                  70                  75                  80

Ala Thr Val Tyr Val Asp Val Leu Lys Asp Ser Gly Arg Asp Tyr Val
                85                  90                  95

Ser Gln Phe Glu Gly Ser Ala Leu Gly Lys Gln Leu Asn Leu Lys Leu
            100                 105                 110

Leu Asp Asn Trp Asp Ser Val Thr Ser Thr Phe Ser Lys Leu Arg Glu
        115                 120                 125

Gln Leu Gly Pro Val Thr Gln Glu Phe Trp Asp Asn Leu Glu Lys Glu
    130                 135                 140

Thr Glu Gly Leu Arg Gln Glu Met Ser Lys Asp Leu Glu Glu Val Lys
145                 150                 155                 160

Ala Lys Val Gln Pro Tyr Leu Asp Asp Phe Gln Lys Lys Trp Gln Glu
                165                 170                 175

Glu Met Glu Leu Tyr Arg Gln Lys Val Glu Pro Leu Arg Ala Glu Leu
            180                 185                 190

Gln Glu Gly Ala Arg Gln Lys Leu His Glu Leu Gln Glu Lys Leu Ser
        195                 200                 205

Pro Leu Gly Glu Glu Met Arg Asp Arg Ala Arg Ala His Val Asp Ala
    210                 215                 220

Leu Arg Thr His Leu Ala Pro Tyr Ser Asp Glu Leu Arg Gln Arg Leu
```

Ala Ala Arg Leu Glu Ala Leu Lys Glu Asn Gly Gly Ala Arg Leu Ala
                245                 250                 255

Glu Tyr His Ala Lys Ala Thr Glu His Leu Ser Thr Leu Ser Glu Lys
                260                 265                 270

Ala Lys Pro Ala Leu Glu Asp Leu Arg Gln Gly Leu Leu Pro Val Leu
                275                 280                 285

Glu Ser Phe Lys Val Ser Phe Leu Ser Ala Leu Glu Glu Tyr Thr Lys
    290                 295                 300

Lys Leu Asn Thr Gln
305

<210> SEQ ID NO 10
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Tetranectin-apolipoprotein A-I fusion
      polypeptide (IVN)

<400> SEQUENCE: 10

Ile Val Asn Ala Lys Lys Asp Val Val Asn Thr Lys Met Phe Glu Glu
1               5                   10                  15

Leu Lys Ser Arg Leu Asp Thr Leu Ala Gln Glu Val Ala Leu Leu Lys
                20                  25                  30

Glu Gln Gln Ala Leu Gln Thr Val Asp Glu Pro Pro Gln Ser Pro Trp
            35                  40                  45

Asp Arg Val Lys Asp Leu Ala Thr Val Tyr Val Asp Val Leu Lys Asp
    50                  55                  60

Ser Gly Arg Asp Tyr Val Ser Gln Phe Glu Gly Ser Ala Leu Gly Lys
65                  70                  75                  80

Gln Leu Asn Leu Lys Leu Leu Asp Asn Trp Asp Ser Val Thr Ser Thr
                85                  90                  95

Phe Ser Lys Leu Arg Glu Gln Leu Gly Pro Val Thr Gln Glu Phe Trp
                100                 105                 110

Asp Asn Leu Glu Lys Glu Thr Glu Gly Leu Arg Gln Glu Met Ser Lys
            115                 120                 125

Asp Leu Glu Glu Val Lys Ala Lys Val Gln Pro Tyr Leu Asp Asp Phe
    130                 135                 140

Gln Lys Lys Trp Gln Glu Glu Met Glu Leu Tyr Arg Gln Lys Val Glu
145                 150                 155                 160

Pro Leu Arg Ala Glu Leu Gln Glu Gly Ala Arg Gln Lys Leu His Glu
                165                 170                 175

Leu Gln Glu Lys Leu Ser Pro Leu Gly Glu Glu Met Arg Asp Arg Ala
                180                 185                 190

Arg Ala His Val Asp Ala Leu Arg Thr His Leu Ala Pro Tyr Ser Asp
            195                 200                 205

Glu Leu Arg Gln Arg Leu Ala Ala Arg Leu Glu Ala Leu Lys Glu Asn
    210                 215                 220

Gly Gly Ala Arg Leu Ala Glu Tyr His Ala Lys Ala Thr Glu His Leu
225                 230                 235                 240

Ser Thr Leu Ser Glu Lys Ala Lys Pro Ala Leu Glu Asp Leu Arg Gln
                245                 250                 255

```
Gly Leu Leu Pro Val Leu Glu Ser Phe Lys Val Ser Phe Leu Ser Ala
            260                 265                 270

Leu Glu Glu Tyr Thr Lys Lys Leu Asn Thr Gln
        275                 280

<210> SEQ ID NO 11
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Tetranectin-apolipoprotein A-I fusion
      polypeptide (PIVN)

<400> SEQUENCE: 11

Pro Ile Val Asn Ala Lys Lys Asp Val Val Asn Thr Lys Met Phe Glu
1               5                   10                  15

Glu Leu Lys Ser Arg Leu Asp Thr Leu Ala Gln Glu Val Ala Leu Leu
            20                  25                  30

Lys Glu Gln Gln Ala Leu Gln Thr Val Asp Glu Pro Pro Gln Ser Pro
        35                  40                  45

Trp Asp Arg Val Lys Asp Leu Ala Thr Val Tyr Val Asp Val Leu Lys
50                  55                  60

Asp Ser Gly Arg Asp Tyr Val Ser Gln Phe Glu Gly Ser Ala Leu Gly
65                  70                  75                  80

Lys Gln Leu Asn Leu Lys Leu Leu Asp Asn Trp Asp Ser Val Thr Ser
                85                  90                  95

Thr Phe Ser Lys Leu Arg Glu Gln Leu Gly Pro Val Thr Gln Glu Phe
            100                 105                 110

Trp Asp Asn Leu Glu Lys Glu Thr Glu Gly Leu Arg Gln Glu Met Ser
        115                 120                 125

Lys Asp Leu Glu Glu Val Lys Ala Lys Val Gln Pro Tyr Leu Asp Asp
130                 135                 140

Phe Gln Lys Lys Trp Gln Glu Glu Met Glu Leu Tyr Arg Gln Lys Val
145                 150                 155                 160

Glu Pro Leu Arg Ala Glu Leu Gln Glu Gly Ala Arg Gln Lys Leu His
                165                 170                 175

Glu Leu Gln Glu Lys Leu Ser Pro Leu Gly Glu Glu Met Arg Asp Arg
            180                 185                 190

Ala Arg Ala His Val Asp Ala Leu Arg Thr His Leu Ala Pro Tyr Ser
        195                 200                 205

Asp Glu Leu Arg Gln Arg Leu Ala Ala Arg Leu Glu Ala Leu Lys Glu
210                 215                 220

Asn Gly Gly Ala Arg Leu Ala Glu Tyr His Ala Lys Ala Thr Glu His
225                 230                 235                 240

Leu Ser Thr Leu Ser Glu Lys Ala Lys Pro Ala Leu Glu Asp Leu Arg
                245                 250                 255

Gln Gly Leu Leu Pro Val Leu Glu Ser Phe Lys Val Ser Phe Leu Ser
            260                 265                 270

Ala Leu Glu Glu Tyr Thr Lys Lys Leu Asn Thr Gln
        275                 280

<210> SEQ ID NO 12
<211> LENGTH: 285
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: Tetranectin-apolipoprotein A-I (XPIVN)
<220> FEATURE:
<221> NAME/KEY: MOD_RES
<222> LOCATION: (1)..(1)
<223> OTHER INFORMATION: Gly, Ser or Thr

<400> SEQUENCE: 12

Xaa Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
        115                 120                 125

Ser Lys Asp Leu Glu Glu Val Lys Ala Lys Val Gln Pro Tyr Leu Asp
130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
        195                 200                 205

Ser Asp Glu Leu Arg Gln Arg Leu Ala Ala Arg Leu Glu Ala Leu Lys
210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
                245                 250                 255

Arg Gln Gly Leu Leu Pro Val Leu Glu Ser Phe Lys Val Ser Phe Leu
            260                 265                 270

Ser Ala Leu Glu Glu Tyr Thr Lys Lys Leu Asn Thr Gln
        275                 280                 285

<210> SEQ ID NO 13
<211> LENGTH: 285
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Tetranectin-apolipoprotein A-I fusion
      polypeptide (APIVN)

<400> SEQUENCE: 13
```

```
Ala Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
        115                 120                 125

Ser Lys Asp Leu Glu Glu Val Lys Ala Lys Val Gln Pro Tyr Leu Asp
    130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
        195                 200                 205

Ser Asp Glu Leu Arg Gln Arg Leu Ala Ala Arg Leu Glu Ala Leu Lys
    210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
                245                 250                 255

Arg Gln Gly Leu Leu Pro Val Leu Glu Ser Phe Lys Val Ser Phe Leu
            260                 265                 270

Ser Ala Leu Glu Glu Tyr Thr Lys Lys Leu Asn Thr Gln
    275                 280                 285

<210> SEQ ID NO 14
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Tetranectin-apolipoprotein A-I fusion
      polypeptide (XIVN) with hexa-histidine-tag
<220> FEATURE:
<221> NAME/KEY: misc_feature
<222> LOCATION: (7)..(23)
<223> OTHER INFORMATION: This region may encompass any of A, G, S, P,
      AP, GP, SP, PP, GSAP, GSGP, GSSP, GSPP, GGGS, GGGGS, GGGSGGGS,
      GGGGSGGGS, GGGSGGGSGGGS, GGGGSGGGGSGGGGS, GGGSAP, GGGSGP, GGGSSP,
      GGGSPP, GGGGSAP, GGGGSGP, GGGGSSP, GGGGSPP, GGGSGGGSAP,
      GGGSGGGSGP,
<220> FEATURE:
<221> NAME/KEY: misc_feature
<222> LOCATION: (7)..(23)
<223> OTHER INFORMATION: Cont'd from above: GGGSGGGSSP, GGGSGGGSPP,
      GGGSGGGSGGGSAP, GGGSGGGSGGGSGP, GGGSGGGSGGGSSP, GGGSGGGSGGGSPP,
```

-continued

```
        GGGGSAP, GGGGSGP, GGGGSSP, GGGGSPP, GGGGSGGGGSAP, GGGGSGGGGSGP,
        GGGGSGGGGSSP, GGGGSGGGGSPP, GGGGSGGGGSGGGGSAP,
<220> FEATURE:
<221> NAME/KEY: misc_feature
<222> LOCATION: (7)..(23)
<223> OTHER INFORMATION: Cont'd from above: GGGGSGGGGSGGGGSGP,
        GGGGSGGGGSGGGGSSP or GGGGSGGGGSGGGGSPP; wherein some positions may
        be absent
<220> FEATURE:
<223> OTHER INFORMATION: See specification as filed for detailed
        description of substitutions and preferred embodiments

<400> SEQUENCE: 14

His His His His His His Xaa Xaa Xaa Xaa Xaa Xaa Xaa Xaa Xaa
1               5                   10                  15

Xaa Xaa Xaa Xaa Xaa Xaa Xaa Ile Val Asn Ala Lys Lys Asp Val Val
                20                  25                  30

Asn Thr Lys Met Phe Glu Glu Leu Lys Ser Arg Leu Asp Thr Leu Ala
            35                  40                  45

Gln Glu Val Ala Leu Leu Lys Glu Gln Gln Ala Leu Gln Thr Val Asp
        50                  55                  60

Glu Pro Pro Gln Ser Pro Trp Asp Arg Val Lys Asp Leu Ala Thr Val
65                  70                  75                  80

Tyr Val Asp Val Leu Lys Asp Ser Gly Arg Asp Tyr Val Ser Gln Phe
                85                  90                  95

Glu Gly Ser Ala Leu Gly Lys Gln Leu Asn Leu Lys Leu Leu Asp Asn
            100                 105                 110

Trp Asp Ser Val Thr Ser Thr Phe Ser Lys Leu Arg Glu Gln Leu Gly
        115                 120                 125

Pro Val Thr Gln Glu Phe Trp Asp Asn Leu Glu Lys Glu Thr Glu Gly
    130                 135                 140

Leu Arg Gln Glu Met Ser Lys Asp Leu Glu Glu Val Lys Ala Lys Val
145                 150                 155                 160

Gln Pro Tyr Leu Asp Asp Phe Gln Lys Lys Trp Gln Glu Glu Met Glu
                165                 170                 175

Leu Tyr Arg Gln Lys Val Glu Pro Leu Arg Ala Glu Leu Gln Glu Gly
            180                 185                 190

Ala Arg Gln Lys Leu His Glu Leu Gln Glu Lys Leu Ser Pro Leu Gly
        195                 200                 205

Glu Glu Met Arg Asp Arg Ala Arg Ala His Val Asp Ala Leu Arg Thr
    210                 215                 220

His Leu Ala Pro Tyr Ser Asp Glu Leu Arg Gln Arg Leu Ala Ala Arg
225                 230                 235                 240

Leu Glu Ala Leu Lys Glu Asn Gly Gly Ala Arg Leu Ala Glu Tyr His
                245                 250                 255

Ala Lys Ala Thr Glu His Leu Ser Thr Leu Ser Glu Lys Ala Lys Pro
            260                 265                 270

Ala Leu Glu Asp Leu Arg Gln Gly Leu Leu Pro Val Leu Glu Ser Phe
        275                 280                 285

Lys Val Ser Phe Leu Ser Ala Leu Glu Glu Tyr Thr Lys Lys Leu Asn
    290                 295                 300

Thr Gln
305

<210> SEQ ID NO 15
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      linker peptide

<400> SEQUENCE: 15

Gly Ser Ala Pro
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 16

Gly Ser Gly Pro
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 17

Gly Ser Ser Pro
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 18

Gly Ser Pro Pro
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 19

Gly Gly Gly Ser
1

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 20

Gly Gly Gly Gly Ser
1               5
```

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 21

Gly Gly Gly Ser Gly Gly Gly Ser
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 22

Gly Gly Gly Gly Ser Gly Gly Gly Gly Ser
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 23

Gly Gly Gly Ser Gly Gly Gly Ser Gly Gly Gly Ser
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 25

Gly Gly Gly Ser Ala Pro
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

```
<400> SEQUENCE: 26

Gly Gly Gly Ser Gly Pro
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 27

Gly Gly Gly Ser Ser Pro
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 28

Gly Gly Gly Ser Pro Pro
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 29

Gly Gly Gly Gly Ser Ala Pro
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 30

Gly Gly Gly Gly Ser Gly Pro
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 31

Gly Gly Gly Gly Ser Ser Pro
1               5

<210> SEQ ID NO 32
<211> LENGTH: 7
<212> TYPE: PRT
```

<213> ORGANISM: Artificial Sequence
<220> FEATURE:
<223> OTHER INFORMATION: Description of Artificial Sequence: Synthetic
      linker peptide

<400> SEQUENCE: 32

Gly Gly Gly Gly Ser Pro Pro
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 33

Gly Gly Gly Ser Gly Gly Gly Ser Ala Pro
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 34

Gly Gly Gly Ser Gly Gly Gly Ser Gly Pro
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 35

Gly Gly Gly Ser Gly Gly Gly Ser Ser Pro
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 36

Gly Gly Gly Ser Gly Gly Gly Ser Pro Pro
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 37

Gly Gly Gly Ser Gly Gly Gly Ser Gly Gly Gly Ser Ala Pro
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 38

Gly Gly Gly Ser Gly Gly Gly Ser Gly Gly Gly Ser Gly Pro
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 39

Gly Gly Gly Ser Gly Gly Gly Ser Gly Gly Gly Ser Ser Pro
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 40

Gly Gly Gly Ser Gly Gly Gly Ser Gly Gly Gly Ser Pro Pro
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 41

Gly Gly Gly Gly Ser Ala Pro
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 42

Gly Gly Gly Gly Ser Gly Pro
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 43

Gly Gly Gly Gly Ser Ser Pro
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 44

Gly Gly Gly Gly Ser Pro Pro
1               5

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 45

Gly Gly Gly Gly Ser Gly Gly Gly Gly Ser Ala Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 46

Gly Gly Gly Gly Ser Gly Gly Gly Gly Ser Gly Pro
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 47

Gly Gly Gly Gly Ser Gly Gly Gly Gly Ser Ser Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 48

Gly Gly Gly Gly Ser Gly Gly Gly Gly Ser Pro Pro
1               5                   10

<210> SEQ ID NO 49
<211> LENGTH: 17

<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 49

Gly Gly Gly Gly Ser Gly Gly Gly Gly Ser Gly Gly Gly Gly Ser Ala
1               5                   10                  15

Pro

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 50

Gly Gly Gly Gly Ser Gly Gly Gly Gly Ser Gly Gly Gly Gly Ser Gly
1               5                   10                  15

Pro

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 51

Gly Gly Gly Gly Ser Gly Gly Gly Gly Ser Gly Gly Gly Gly Ser Ser
1               5                   10                  15

Pro

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 52

Gly Gly Gly Gly Ser Gly Gly Gly Gly Ser Gly Gly Gly Gly Ser Pro
1               5                   10                  15

Pro

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-terminal amino acid sequence of the shortened
      by-product

<400> SEQUENCE: 53

Val Ala Arg Arg Asn Gly Thr Val Gln Thr Glu Ser
1               5                   10

```
<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Human interferon fragment

<400> SEQUENCE: 54

Cys Asp Leu Pro Gln Thr His Ser Leu
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 55

His His His His His His
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: IgA protease cleavage site

<400> SEQUENCE: 56

Val Val Ala Pro Pro Ala Pro
1               5

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Ile Val Asn
1

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly, Ser or Thr

<400> SEQUENCE: 58

Xaa Pro Ile Val Asn
1               5

<210> SEQ ID NO 59
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Pro Ile Val Asn
1               5

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(25)

<400> SEQUENCE: 60 a gaa aac ggt ggt gcg agg cta gcg gaataccacg caaaa          40
  Glu Asn Gly Gly Ala Arg Leu Ala
  1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Asn Gly Gly Ala Arg Leu Ala
1               5

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(19)

<400> SEQUENCE: 62 a gaa aac ggt ggt gcg ggc tag                               22
  Glu Asn Gly Gly Ala Gly
  1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Asn Gly Gly Ala Gly
1               5
```

METHOD FOR REDUCTION OF 1→2 READING FRAME SHIFTS

CROSS REFERENCE TO RELATED APPLICATIONS

This application is a continuation of International Application No. PCT/EP2013/053547 having an international filing date of Feb. 22, 2013, the entire contents of which are incorporated herein by reference, and which claims benefit under 35 U.S.C. §119 to European Patent Application Nos. 12157512.0 filed Feb. 29, 2012 and 12162810.1 filed Apr. 2, 2012.

SEQUENCE LISTING

The instant application contains a Sequence Listing submitted via EFS-Web and hereby incorporated by reference in its entirety. Said ASCII copy, created on Oct. 2, 2014, is named P4891C1-US SL.txt, and is 33,559 bytes in size.

FIELD OF THE INVENTION

The current invention is in the field of recombinant polypeptide production. It is reported herein a method for recombinantly producing a polypeptide with reduced by-product content wherein the reduction of the by-product content is achieved by a modification of the encoding nucleic acid that reduces frameshifts during the translation or transcription process.

BACKGROUND OF THE INVENTION

Proteins play an important role in today's medical portfolio. For human application every pharmaceutical substance has to meet distinct criteria. To ensure the safety of biopharmaceutical agents to humans nucleic acids, viruses, and host cell proteins, which would cause severe harm, have to be removed especially. To meet the regulatory specification one or more purification steps have to follow the manufacturing process.

Recombinant polypeptides can be produced e.g. by prokaryotic cells such as *E. coli*. The recombinantly produced polypeptide accounts for the majority of the prokaryotic cell's polypeptide content and is often deposited as insoluble aggregate, i.e. as a so called inclusion body, within the prokaryotic cell. For the isolation of the recombinant polypeptide the cells have to be disintegrated and the recombinant polypeptide contained in the inclusion bodies has to be solubilized after the separation of the inclusion bodies from the cell debris. For the solubilization chaotropic reagents, such as urea or guanidinium chloride, are used. To cleave disulfide bonds reducing agents, especially under alkaline conditions, such as dithioerythritol, dithiothreitol, or β-mercaptoethanol are added. After the solubilization of the aggregated polypeptide the globular structure of the recombinant polypeptide, which is essential for the biological activity, has to be reestablished. During this so called renaturation process the concentration of the denaturing agents is (slowly) reduced, e.g. by dialysis against a suited buffer, which allows the denatured polypeptide to refold into its biologically active structure. After renaturation the recombinant polypeptide is purified to a purity acceptable for the intended use. For example, for the use as a therapeutic protein a purity of more than 90% has to be established.

Recombinantly produced polypeptides are normally accompanied by nucleic acids, endotoxins, and/or polypeptides from the producing cell. Beside the host cell derived by-products also polypeptide-derived by-products are present in a crude polypeptide preparation. Among others shortened variants of the polypeptide of interest can be present.

In WO 95/25786 the production of human apolipoprotein A1 in a bacterial expression system is reported.

SUMMARY OF THE INVENTION

It has been found that the oligonucleotide that encodes the dipeptide AR can be the point of a 1→2 frameshift during the translation or transcription process of a nucleic acid that encodes a polypeptide which comprises the dipeptide AR. Due to the occurrence of the frameshift a nonsense polypeptide with a not-encoded amino acid sequence is produced.

Thus, it has been found that the oligonucleotide encoding the dipeptide AR which is comprised in a nucleic acid encoding a larger polypeptide should be selected from the oligonucleotides gca cgt (SEQ ID NO: 03), gcg cgt (SEQ ID NO: 04), and gcc cgt (SEQ ID NO: 05). It has been found that the fourth nucleotide in the oligonucleotide encoding the dipeptide AR should not be 'a'.

One aspect as reported herein is a method for the recombinant production of a polypeptide, which comprises the dipeptide AR (SEQ ID NO: 06), characterized in that the method comprises the following step:
    recovering the polypeptide from the cells or the cultivation medium of a cultivation of a cell comprising a nucleic acid encoding the polypeptide and thereby producing the polypeptide,
whereby the oligonucleotide encoding the dipeptide AR comprised in the nucleic acid encoding the polypeptide has the nucleotide 'c' at the fourth position.

Thus, herein is reported as one aspect a method for the recombinant production of a polypeptide, which comprises the dipeptide AR (SEQ ID NO: 06), characterized in that the method comprises the following step:
    recovering the polypeptide from the cells or the cultivation medium of a cultivation of a cell comprising a nucleic acid encoding the polypeptide and thereby producing the polypeptide,
whereby the dipeptide AR comprised in the polypeptide is encoded by the oligonucleotide gca cgt (SEQ ID NO: 03), or the oligonucleotide gcg cgt (SEQ ID NO: 04), or the oligonucleotide gcc cgt (SEQ ID NO: 05).

One aspect as reported herein is a method for the reduction of by-product formation by a 1→2 frameshift in the production of a polypeptide, which comprises the dipeptide AR (SEQ ID NO: 06), characterized in that the method comprises the following step:
    recovering the polypeptide from the cells or the cultivation medium of a cultivation of a cell comprising a nucleic acid encoding the polypeptide and thereby producing the polypeptide,
whereby the oligonucleotide encoding the dipeptide AR comprised in the nucleic acid encoding the polypeptide has the nucleotide 'c' at the fourth position.

Thus, herein is reported as one aspect a method for reducing the by-product formation by 1→2 frameshift in the recombinant production of a polypeptide, which comprises the dipeptide AR (SEQ ID NO: 06), characterized in that the method comprises the following step:
    recovering the polypeptide from the cells or the cultivation medium of a cultivation of a cell comprising a nucleic acid encoding the polypeptide and thereby producing the polypeptide, whereby the dipeptide AR comprised in the polypeptide is encoded by the oligonucleotide gca cgt (SEQ ID NO: 03), or the oligonucleotide gcg cgt (SEQ ID NO: 04), or the oligonucleotide gcc cgt (SEQ ID NO: 05).

In one embodiment of all aspects as reported before the dipeptide AR is all dipeptides AR.

In one embodiment of all aspects as reported herein the dipeptide AR is the last dipeptide AR in the amino acid sequence.

One aspect as reported herein is a method for the recombinant production of an apolipoprotein A-I of SEQ ID NO: 09 or SEQ ID NO: 11, which comprises the dipeptide AR (SEQ ID NO: 06), characterized in that the method comprises the following step:

recovering the apolipoprotein A-I from the cells or the cultivation medium of a cultivation of a cell comprising a nucleic acid encoding the apolipoprotein A-I of SEQ ID NO: 09 or SEQ ID NO: 11 and thereby producing the apolipoprotein A-I, whereby the oligonucleotide encoding the last dipeptide AR comprised in the nucleic acid encoding the apolipoprotein A-I has the nucleotide 'c' at the fourth position.

Thus, herein is reported as one aspect a method for the recombinant production of an apolipoprotein A-I of SEQ ID NO: 09 or SEQ ID NO: 11, which comprises the dipeptide AR (SEQ ID NO: 06), characterized in that the method comprises the following step:

recovering the apolipoprotein A-I from the cells or the cultivation medium of a cultivation of a cell comprising a nucleic acid encoding the apolipoprotein A-I of SEQ ID NO: 09 or SEQ ID NO: 11 and thereby producing the apolipoprotein, whereby the last dipeptide AR comprised in the apolipoprotein A-I amino acid sequence is encoded by the oligonucleotide gca cgt (SEQ ID NO: 03), or the oligonucleotide gcg cgt (SEQ ID NO: 04), or the oligonucleotide gcc cgt (SEQ ID NO: 05).

One aspect as reported herein is a nucleic acid encoding a polypeptide that comprises the dipeptide AR in its amino acid sequence whereby the dipeptide AR is encoded by the oligonucleotide gca cgt (SEQ ID NO: 03), or the oligonucleotide gcg cgt (SEQ ID NO: 04), or the oligonucleotide gcc cgt (SEQ ID NO: 05).

One aspect as reported herein is a cell comprising a nucleic acid as reported herein.

One aspect as reported herein is the use of the oligonucleotide gca cgt (SEQ ID NO: 03), or the oligonucleotide gcg cgt (SEQ ID NO: 04), or the oligonucleotide gcc cgt (SEQ ID NO: 05) for encoding the dipeptide AR comprised in a polypeptide.

In the following embodiments of all aspects as reported herein are specified.

In one embodiment the dipeptide AR is encoded by the oligonucleotide gca cgt (SEQ ID NO: 03).

In one embodiment the dipeptide AR is encoded by the oligonucleotide gcg cgt (SEQ ID NO: 04).

In one embodiment the dipeptide AR is encoded by the oligonucleotide gcc cgt (SEQ ID NO: 05).

In one embodiment the polypeptide comprises about 50 amino acid residues to about 500 amino acid residues. In one embodiment the polypeptide comprises about 100 amino acid residues to about 400 amino acid residues. In one embodiment the polypeptide comprises about 250 amino acid residues to about 350 amino acid residues.

In one embodiment the cell is a prokaryotic cell. In one embodiment the prokaryotic cell is an *E. coli* cell, or a *bacillus* cell.

In one embodiment the cell is a eukaryotic cell. In one embodiment the cell is a CHO cell, or a HEK cell, or a BHK cell, or a NS0 cell, or a SP2/0 cell, or a yeast cell.

In one embodiment the polypeptide is a hetero-multimeric polypeptide. In one embodiment the polypeptide is an antibody or an antibody fragment.

In one embodiment the polypeptide is a homo-multimeric polypeptide. In one embodiment the polypeptide is a homo-dimer or a homo-trimer.

In one embodiment the polypeptide is human apolipoprotein A-I or a variant thereof having the biological activity of human apolipoprotein A-I. In one embodiment the apolipoprotein A-I variant has the amino acid sequence selected from the group of SEQ ID NO: 09 to SEQ ID NO: 14.

In one embodiment the polypeptide is human apolipoprotein A-I that has the amino acid sequence of SEQ ID NO: 09 or SEQ ID NO: 11.

DETAILED DESCRIPTION OF THE INVENTION

Definitions:

The term "amino acid" denotes the group of carboxy α-amino acids, which directly or in form of a precursor can be encoded by nucleic acid. The individual amino acids are encoded by nucleic acids consisting of three nucleotides, so called codons or base-triplets. Each amino acid is encoded by at least one codon. The encoding of the same amino acid by different codons is known as "degeneration of the genetic code". The term "amino acid" denotes the naturally occurring carboxy α-amino acids and comprises alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "apolipoprotein A-I" denotes an amphiphilic, helical polypeptide with protein-lipid and protein-protein interaction properties. Apolipoprotein A-I is synthesized by the liver and small intestine as prepro-apolipoprotein of 267 amino acid residues which is secreted as a pro-apolipoprotein that is cleaved to the mature polypeptide having 243 amino acid residues. Apolipoprotein A-I consists of 6 to 8 different amino acid repeats consisting each of 22 amino acid residues separated by a linker moiety which is often proline, and in some cases consists of a stretch made up of several residues. An exemplary human apolipoprotein A-I amino acid sequence is reported in GenPept database entry NM-000039 or database entry X00566; GenBank NP-000030.1 (gi 4557321). Of human apolipoprotein A-I (SEQ ID NO: 07) naturally occurring variants exist, such as P27H, P27R, P28R, R34L, G50R, L84R, D113E, A-A119D, D127N, deletion of K131, K131M, W132R, E133K, R151C (amino acid residue 151 is changed from Arg to Cys, apolipoprotein A-I-Paris), E160K, E163G, P167R, L168R, E171V, P189R, R197C (amino acid residue 173 is change from Arg to Cys, apolipoprotein A-I-Milano) and E222K. Also included are variants that have conservative amino acid modifications.

The term "codon" denotes an oligonucleotide consisting of three nucleotides that encodes a defined amino acid. Due to the degeneracy of the genetic code some amino acids are encoded by more than one codon. These different codons encoding the same amino acid have different relative usage frequencies in individual host cells. Thus, a specific amino acid can be encoded by a group of different codons. Likewise the amino acid sequence of a polypeptide can be encoded by different nucleic acids. Therefore, a specific amino acid can be encoded by a group of different codons, whereby each of these codons has a usage frequency within a given host cell.

TABLE

*Escherichia Coli* codon usage
(codon | encoded amino acid | usage frequency [%])

| | | | | | | | | | | | |
|---|---|---|---|---|---|---|---|---|---|---|---|
| TTT | F | 58 | TCT | S | 17 | TAT | Y | 59 | TGT | C | 46 |
| TTC | F | 42 | TCC | S | 15 | TAC | Y | 41 | TGC | C | 54 |
| TTA | L | 14 | TCA | S | 14 | TAA | * | 61 | TGA | * | 30 |
| TTG | L | 13 | TCG | S | 14 | TAG | * | 9 | TGG | W | 100 |
| CTT | L | 12 | CCT | P | 18 | CAT | H | 57 | CGT | R | 36 |
| CTC | L | 10 | CCC | P | 13 | CAC | H | 43 | CGC | R | 36 |
| CTA | L | 4 | CCA | P | 20 | CAA | Q | 34 | CGA | R | 7 |
| CTG | L | 47 | CCG | P | 49 | CAG | Q | 66 | CGG | R | 11 |
| ATT | I | 49 | ACT | T | 19 | AAT | N | 49 | AGT | S | 16 |
| ATC | I | 39 | ACC | T | 40 | AAC | N | 51 | AGC | S | 25 |
| ATA | I | 11 | ACA | T | 17 | AAA | K | 74 | AGA | R | 7 |
| ATG | M | 100 | ACG | T | 25 | AAG | K | 26 | AGG | R | 4 |
| GTT | V | 28 | GCT | A | 18 | GAT | D | 63 | GGT | G | 35 |
| GTC | V | 20 | GCC | A | 26 | GAC | D | 37 | GGC | G | 37 |
| GTA | V | 17 | GCA | A | 23 | GAA | E | 68 | GGA | G | 13 |
| GTG | V | 35 | GCG | A | 33 | GAG | E | 32 | GGG | G | 15 |

Conservative substitutions are shown in the following Table under the heading of "preferred substitutions". Additional more substantial changes are provided in the following Table under the heading of "exemplary substitutions," and as further described below in reference to amino acid side chain classes

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Non-conservative substitutions will entail exchanging a member of one of these classes for another class.

The term "conservative amino acid modification" denotes modifications of the amino acid sequence which do not affect or alter the characteristics of the polypeptide. Modifications can be introduced by standard techniques known in the art, such as site-directed mutagenesis and PCR-mediated mutagenesis. Conservative amino acid modifications include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), non-polar side chains (e.g. alanine, valine, leucine, isoleucine, proline, phenylalanine, methionine), beta-branched side chains (e.g. threonine, valine, isoleucine), and aromatic side chains (e.g. tyrosine, phenylalanine, tryptophan, histidine).

The term "variant of a polypeptide" denotes a polypeptide which differs in amino acid sequence from a "parent" polypeptide's amino acid sequence by up to ten, in one embodiment from about two to about five, additions, deletions, and/or substitutions. Amino acid sequence modifications can be performed by mutagenesis based on molecular modeling as described by Riechmann, L., et al., Nature 332 (1988) 323-327, and Queen, C., et al., Proc. Natl. Acad. Sci. USA 86 (1989) 10029-10033.

The homology and identity of different amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90. In one embodiment the algorithm is BLOSUM 30.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The terms "nucleic acid" and "nucleic acid sequence" denote a polymeric molecule consisting of the individual nucleotides (also called bases) 'a', 'c', 'g', and 't' (or 'u' in RNA), i.e. to DNA, RNA, or modifications thereof. This polynucleotide molecule can be a naturally occurring polynucleotide molecule or a synthetic polynucleotide molecule or a combination of one or more naturally occurring polynucleotide molecules with one or more synthetic polynucleotide molecules. Also encompassed by this definition are naturally occurring polynucleotide molecules in which one or more nucleotides are changed (e.g. by mutagenesis), deleted, or added. A nucleic acid can either be isolated, or integrated in another nucleic acid, e.g. in an expression cassette, a plasmid, or the chromosome of a host cell. A nucleic acid is characterized by its nucleic acid sequence consisting of individual nucleotides. The term "oligonucleotide" denotes a polymeric molecule consisting of at most 10 individual nucleotides (also called bases) 'a', 'c', 'g', and 't' (or 'u' in RNA).

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "recombinant polypeptide" and "recombinantly produced polypeptide" denote a polypeptide that is prepared, expressed, or created by recombinant means, such as polypeptides isolated from host cells, such as *E. coli*, NS0, BHK, or CHO cells.

The term "substituting" denotes the change of one specific nucleotide in a parent nucleic acid to obtain a substituted/changed nucleic acid.

The Method as Reported Herein:

Methods and techniques known to a person skilled in the art, which are useful for carrying out the current invention, are described e.g. in Ausubel, F. M. (ed.), Current Protocols in Molecular Biology, Volumes I to III (1997), Wiley and Sons; Sambrook, J., et al., Molecular Cloning: A Laboratory Manual, Second Edition, Cold Spring Harbor Laboratory Press, Cold Spring Harbor, N.Y. (1989); Morrison, S. L., et al., Proc. Natl. Acad. Sci. USA 81 (1984) 6851-6855; U.S. Pat. No. 5,202,238 and U.S. Pat. No. 5,204,244.

It has been found that the oligonucleotide that encodes the dipeptide AR which is comprised in a nucleic acid encoding a polypeptide that comprises the dipeptide AR can be the point of a 1→2 frameshift (mutation) during the transcription or translation process of the nucleic acid that encodes the polypeptide which comprises the dipeptide AR. Due to the occurrence of the frameshift a polypeptide with a not-encoded amino acid sequence, most probably a nonsense or shortened amino acid sequence, is produced.

In more detail, it has been found that depending on the oligonucleotide, which encodes the dipeptide AR and which is comprised in a larger, i.e. an at least 50 amino acid residue, polypeptide encoding nucleic acid, a 1→2 frameshift during the transcription or translation process of the oligonucleotide occurs with different frequency (see the following Table).

TABLE

| AR dipeptide encoding oligonucleotide | 1→2 frameshift occurrence |
|---|---|
| gcg agg (SEQ ID NO: 01) | yes |
| gcg aga (SEQ ID NO: 02) | 30% |
| gca cgt (SEQ ID NO: 03) | below detection limit |
| gcg cgt (SEQ ID NO: 04) | below detection limit |
| gcc cgt (SEQ ID NO: 05) | below detection limit |

Thus, one aspect as reported herein is a method for the recombinant production of a polypeptide, which comprises the dipeptide AR (SEQ ID NO: 06), characterized in that the method comprises the following step:

recovering the polypeptide from the cells or the cultivation medium of a cultivation of a cell comprising a nucleic acid encoding the polypeptide and thereby producing the polypeptide, whereby the dipeptide AR comprised in the polypeptide is encoded by the oligonucleotide gca cgt (SEQ ID NO: 03), or the oligonucleotide gcg cgt (SEQ ID NO: 04), or the oligonucleotide gcc cgt (SEQ ID NO: 05).

Thus, one aspect as reported herein is a method for the recombinant production of a polypeptide, which comprises the dipeptide AR (SEQ ID NO: 06), characterized in that the method comprises the following step:

recovering the polypeptide from the cells or the cultivation medium of a cultivation of a cell comprising a nucleic acid encoding the polypeptide and thereby producing the polypeptide, whereby the oligonucleotide encoding the dipeptide AR comprised in the nucleic acid encoding the polypeptide has the nucleotide 'c' at the fourth position.

In one embodiment the oligonucleotide encoding the dipeptide AR comprises as codon encoding the amino acid A a codon selected from gct, gcc, gca and gcg and as codon encoding the amino acid R a codon selected from cgt, cgc, cga and cgg.

In one embodiment the oligonucleotide encoding the dipeptide AR is selected from the group comprising the oligonucleotides gct cgt, gct cgc, gct cga, gct cgg, gcc cgt, gcc cgc, gcc cga, gcc cgg, gca cgt, gca cgc, gca cga, gca cgg, gcg cgt, gcg cgc, gcg cga, and gcg cgg.

In one embodiment the oligonucleotide encoding the dipeptide AR is selected from the group comprising the oligonucleotides gca cgt (SEQ ID NO: 03), gcg cgt (SEQ ID NO: 04), and gcc cgt (SEQ ID NO: 05).

In one embodiment the method comprises the following steps:

providing a cell comprising a nucleic acid encoding the polypeptide, cultivating the cell (under conditions which are suitable for the expression of the polypeptide), recovering the polypeptide from the cell or the cultivation medium.

optionally purifying the produced polypeptide with one or more chromatography steps.

In one embodiment the polypeptide encoding nucleic acid comprising the dipeptide AR encoding oligonucleotide gca cgt (SEQ ID NO: 03), or the oligonucleotide gcg cgt (SEQ ID NO: 04), or the oligonucleotide gcc cgt (SEQ ID NO: 05) is obtained by substituting two to three nucleotides in the dipeptide AR encoding oligonucleotide gcg agg (SEQ ID NO: 01), or the oligonucleotide gcg aga (SEQ ID NO: 02) to obtain the oligonucleotide gca cgt (SEQ ID NO: 03), or the oligonucleotide gcg cgt (SEQ ID NO: 04), or the oligonucleotide gcc cgt (SEQ ID NO: 05).

In one embodiment the produced polypeptide is purified with one to five chromatography steps. In one embodiment the produced polypeptide is purified with two to four chromatography steps. In one embodiment the produced polypeptide is purified with three chromatography steps.

General chromatographic methods and their use are known to a person skilled in the art. See for example, Chromatography, 5$^{th}$ edition, Part A: Fundamentals and Techniques, Heftmann, E. (ed.), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (ed.), Molecular Cloning: A Laboratory Manual, Second Edition, Cold Spring Harbor Laboratory Press, Cold Spring Harbor, N.Y., (1989); or Current Protocols in Molecular Biology, Ausubel, F. M., et al. (ed.), John Wiley & Sons, Inc., New York.

One aspect as reported herein is a nucleic acid encoding a polypeptide that comprises the dipeptide AR in its amino acid sequence, whereby the dipeptide AR is encoded by the oligonucleotide gca cgt (SEQ ID NO: 03), or the oligonucleotide gcg cgt (SEQ ID NO: 04), or the oligonucleotide gcc cgt (SEQ ID NO: 05).

One aspect as reported herein is a cell comprising a nucleic acid as reported herein.

One aspect as reported herein is the use of the oligonucleotide gca cgt (SEQ ID NO: 03), or the oligonucleotide gcg cgt (SEQ ID NO: 04), or the oligonucleotide gcc cgt (SEQ ID NO: 05) for encoding the dipeptide AR comprised in a polypeptide.

One aspect as reported herein is a method for reducing the by-product formation during the recombinant production of a polypeptide, which comprises the dipeptide AR, comprising the step of:

substituting in the polypeptide encoding nucleic acid two to three nucleotides in the dipeptide AR encoding oligonucleotide gcg agg (SEQ ID NO: 01), or the oligonucleotide gcg aga (SEQ ID NO: 02) to obtain the oligonucleotide gca cgt (SEQ ID NO: 03), or the oligonucleotide gcg cgt (SEQ ID NO: 04), or the oligonucleotide gcc cgt (SEQ ID NO: 05), thereby producing a substituted polypeptide encoding nucleic acid, and recovering the polypeptide from the cells or the cultivation medium of a cultivation of a cell comprising the substituted nucleic acid encoding the polypeptide and thereby reducing the by-product formation during the recombinant production of a polypeptide, which comprises the dipeptide AR.

One aspect as reported herein is a method for increasing the expression of a recombinantly produced polypeptide, which comprises the dipeptide AR, comprising the step of:

substituting in the polypeptide encoding nucleic acid two to three nucleotides in the dipeptide AR encoding oligonucleotide gcg agg (SEQ ID NO: 01), or the oligonucleotide gcg aga (SEQ ID NO: 02) to obtain the oligonucleotide gca cgt (SEQ ID NO: 03), or the oligonucleotide gcg cgt (SEQ ID NO: 04), or the oligonucleotide gcc cgt (SEQ ID NO: 05), thereby producing a substituted polypeptide encoding nucleic acid, and recovering the polypeptide from the cells or the cultivation medium of a cultivation of a cell comprising the substituted nucleic acid encoding the polypeptide and thereby increasing the expression of the polypeptide, which comprises the dipeptide AR.

In one embodiment the method comprises one or more of the following further steps:

providing the amino acid sequence or the encoding nucleic acid of a polypeptide comprising the dipeptide AR, and/or transfecting a cell with the substituted nucleic acid encoding the polypeptide, and/or cultivating the cell transfected with the substituted nucleic acid (under conditions which are suitable for the expression of the polypeptide), and/or recovering the polypeptide from the cell or the cultivation medium, and/or optionally purifying the produced polypeptide with one or more chromatography steps.

In one embodiment the produced polypeptide is purified with one to five chromatography steps. In one embodiment the produced polypeptide is purified with two to four chromatography steps. In one embodiment the produced polypeptide is purified with three chromatography steps.

The method as reported herein is exemplified in the following with a recombinant polypeptide produced in a prokaryotic cell, i.e. a tetranectin-apolipoprotein A-I fusion polypeptide produced in *E. coli*.

The tetranectin-apolipoprotein A-I fusion polypeptide comprises (in N- to C-terminal direction) the human tetranectin trimerising structural element and wild-type human apolipoprotein A-I. The amino acid sequence of the human tetranectin trimerising structural element can be shortened by the first 9 amino acids, thus, starting with the isoleucine residue of position 10, a naturally occurring truncation site. As a consequence of this truncation the O-glycosylation site at threonine residue of position 4 has been deleted. Between the tetranectin trimerising structural element and the human apolipoprotein A-I the five amino acid residues SLKGS (SEQ ID NO: 08) were removed.

For improved expression and purification a construct can be generated comprising an N-terminal purification tag, e.g. a hexahistidine-tag (SEQ ID NO: 55), and a protease cleavage site for removal of the purification tag. In one embodiment the protease is IgA protease and the protease cleavage site is an IgA protease cleavage site. As a result of the specific cleavage of the protease some amino acid residues of the protease cleavage site are retained at the N-terminus of the polypeptide, i.e. in case of an IgA protease cleavage site two amino acid residues—as first alanine or glycine or serine or threonine and as second proline—are maintained at the N-terminus of the polypeptide, e.g. the tetranectin-apolipoprotein A-I fusion polypeptide.

The tetranectin trimerising structural element provides for a domain that allows for the formation of a tetranectin-apolipoprotein A-I homo-trimer that is constituted by non-covalent interactions between each of the individual tetranectin-apolipoprotein A-I monomers.

In one embodiment the apolipoprotein A-I fusion polypeptide is a variant comprising conservative amino acid substitutions.

In one embodiment the tetranectin-apolipoprotein A-I fusion polypeptide comprises an expression and purification tag and has the amino acid sequence of CDLPQTHSLG-SHHHHHHGSVVAPPAPIVNAKKDVVNTKMFEELK-SRLDTLAQEVALLK EQQALQTVDEPPQSPWDRVKD-LATVYVDVLKDSGRDYVSQFEGSALGKQLNLKLLDN WDSVTSTFSKLREQLGPVTQEFWDNLEKETEGL-RQEMSKDLEEVKAKVQPYLDDFQKK WQEEME-LYRQKVEPLRAELQEGARQKLHELQEKLSPL-GEEMRDRARAHVDALRTHLA PYSDELRQRLAARLEALKENGGARLAEYHAKATE-HLSTLSEKAKPALEDLRQGLLPVLE SFKVSFLSAL-EEYTKKLNTQ (SEQ ID NO: 09).

In one embodiment the tetranectin-apolipoprotein A-I fusion polypeptide (IVN) has the amino acid sequence of IVNAKKDVVNTKMFEELKSRLDT-LAQEVALLKEQQALQTVDEPPQSPWDRVKDLATVY VDVLKDSGRDYVSQFEGSALGKQLNLKLLDNWDS-VTSTFSKLREQLGPVTQEFWDNLE KETEGLRQEM-SKDLEEVKAKVQPYLDDFQKKWQEEMELYRQKVE-PLRAELQEGARQK LHELQEKLSPLGEEMRDRARAHVDALRTHLAPYS-DELRQRLAARLEALKENGGARLAE YHAKATEHL-STLSEKAKPALEDLRQGLLPVLESFKVSFLSALEEYT-KKLNTQ (SEQ ID NO: 10).

Thus, in one embodiment the tetranectin-apolipoprotein A-I fusion polypeptide (PIVN) SEQ ID NO: 57) has the amino acid sequence of PIVNAKKDVVNTKMFEELK-SRLDTLAQEVALLKEQQALQTVDEPPQSPWDRVKD-LATVYVDVL KDSGRDYVSQFEGSALGKQLNLKLLD-NWDSVTSTFSKLREQLGPVTQEFWDNLEKETEGLRQ EMSKDLEEVKAKVQPYLDDFQKKWQEEMELYRQK-VEPLRAELQEGARQKLHELQEKLSPLGE EMRDR-ARAHVDALRTHLAPYSDELRQRLAARLEALKENG-GARLAEYHAKATEHLSTLSEKAKP ALEDLRQGLLPVLESFKVSFLSALEEYTKKLNTQ (SEQ ID NO: 11).

In one embodiment the tetranectin-apolipoprotein A-I fusion polypeptide (XPIVN) (SEQ ID NO: 58) has the amino acid sequence of (G,S,T)PIVNAKKDVVNTKM-FEELKSRLDTLAQEVALLKEQQALQTVDEPPQSPW-DRVKDLATV YVDVLKDSGRDYVSQFEGSALG-KQLNLKLLDNWDSVTSTFSKLREQLGPVTQEFWDN LEKET EGLRQEMSKDLEEVKAKVQPYLDDFQK-KWQEEMELYRQKVEPLRAELQEGARQKLHELQEKL SPLGEEMRDRARAHVDALRTHLAPYSDELRQR-LAARLEALKENGGARLAEYHAKATEHLSTLS EKAK-PALEDLRQGLLPVLESFKVSFLSALEEYTKKLNTQ (SEQ ID NO: 12).

Thus, in one embodiment the tetranectin-apolipoprotein A-I fusion polypeptide (APIVN) SEQ ID NO: 59) has the amino acid sequence of APIVNAKKDVVNTKMFEELK-SRLDTLAQEVALLKEQQALQTVDEPPQSPWDRVKD-LATVYVDV LKDSGRDYVSQFEGSALGKQLNLKLLD-NWDSVTSTFSKLREQLGPVTQEFWDNLEKETEGLR QEMSKDLEEVKAKVQPYLDDFQKKWQEEME-LYRQKVEPLRAELQEGARQKLHELQEKLSPLG EEMRDRARAHVDALRTHLAPYSDELRQRLAARLE-ALKENGGARLAEYHAKATEHLSTLSEKAK PALEDL-RQGLLPVLESFKVSFLSALEEYTKKLNTQ (SEQ ID NO: 13).

In one embodiment the tetranectin-apolipoprotein A-I fusion polypeptide (XIVN) comprising a hexa-histidine-tag (SEQ ID NO: 55) has the amino acid sequence of HHHH-HHXIVNAKKDVVNTKMFEELKSRLDT-LAQEVALLKEQQALQTVDEPPQSPWDRVKDLAT VYVDVLKDSGRDYVSQFEGSALGKQLNLKLLDN-WDSVTSTFSKLREQLGPVTQEFWDNLEKE TEGL-RQEMSKDLEEVKAKVQPYLDDFQKKWQEEME-LYRQKVEPLRAELQEGARQKLHELQEK LSPLGEEMRDRARAHVDALRTHLAPYSDELRQR-LAARLEALKENGGARLAEYHAKATEHLSTL SEKAK-PALEDLRQGLLPVLESFKVSFLSALEEYTKKLNTQ (SEQ ID NO: 14), wherein X can be any of the following amino acid sequences A, G, S, P, AP, GP, SP, PP, GSAP (SEQ ID NO: 15), GSGP (SEQ ID NO: 16), GSSP (SEQ ID NO: 17), GSPP (SEQ ID NO: 18), GGGS (SEQ ID NO: 19), GGGGS (SEQ ID NO: 20), GGGSGGG (SEQ ID NO: 21), GGGGSGGGGS (SEQ ID NO: 22), GGGSGGGSGGGS (SEQ ID NO: 23), GGGGSGGGGSGGGGS (SEQ ID NO: 24), GGGSAP (SEQ ID NO: 25), GGGSGP (SEQ ID NO: 26), GGGSSP (SEQ ID NO: 27), GGGSPP (SEQ ID NO: 28), GGGGSAP (SEQ ID NO: 29), GGGGSGP (SEQ ID NO: 30), GGGGSSP (SEQ ID NO: 31), GGGGSPP (SEQ ID NO: 32), GGGSGGGSAP (SEQ ID NO: 33), GGGSGGGSGP (SEQ ID NO: 34), GGGSGGGSSP (SEQ ID NO: 35), GGGSGGGSPP (SEQ ID NO: 36), GGGSGGGSGGGSAP (SEQ ID NO: 37), GGGSGGGSGGGSGP (SEQ ID NO: 38), GGGSGGGSGGGSSP (SEQ ID NO: 39), GGGSGGGSGGGSPP (SEQ ID NO: 40), GGGGSAP (SEQ ID NO: 41), GGGGSGP (SEQ ID NO: 42), GGGGSSP (SEQ ID NO: 43), GGGGSPP (SEQ ID NO: 44), GGGGSGGGGSAP (SEQ ID NO: 45), GGGGSGGGGSGP (SEQ ID NO: 46), GGGGSGGGGSSP (SEQ ID NO: 47), GGGGSGGGGSPP (SEQ ID NO: 48), GGGGSGGGGSGGGGSAP (SEQ ID NO: 49), GGGGSGGGGSGGGGSGP (SEQ ID NO: 50), GGGGSGGGGSGGGGSSP (SEQ ID NO: 51), and GGGGSGGGGSGGGGSPP (SEQ ID NO: 52).

It has to be noted that if a polypeptide is recombinantly produced in *E. coli* strains the N-terminal methionine residue is usually not efficiently cleaved off by *E. coli* proteases. Thus, the N-terminal methionine residue is partially present in the produced polypeptide.

A tetranectin-apolipoprotein A-I fusion polypeptide of SEQ ID NO: 09 was recombinantly produced in *E. coli*. A main by-product could be detected.

Via Edmann sequencing and Lys-C peptide mapping (LC-ESI-MS/MS) the N-terminal amino acid sequence after the IgA protease cleavage was detected. The sequence corresponds to the N-terminal amino acid sequence of the tetranectin-apolipoprotein A-I fusion polypeptide (APIVNAKKDVVN=amino acid residues 1-12 of SEQ ID NO: 13).

Via top-down MS the full length C-terminal amino acid fragment corresponding to SEQ ID NO: 13 could not be detected. Fragments corresponding to residues 1 to 105 of SEQ ID NO: 13 could be found.

Via Lys-C peptide mapping (LC-ESI-MS/MS) the C-terminal peptide could also not be detected. All peptides from amino acid residue 1 to 224 of SEQ ID NO: 13 could be observed.

Thus, the deviation from the encoding nucleic acid occurs in the amino acid range from residue 225 to residue 230 of SEQ ID NO: 13.

It has been found that the deviation from the intended amino acid sequence occurred at position 760 at the nucleotide 'a' of the nucleic acid encoding the tetranectin-apolipoprotein A-I fusion polypeptide with an amino acid sequence of SEQ ID NO: 09 (corresponding to amino acid position 254 of SEQ ID NO: 09), which is not processed during the transcription or translation process.

The deviation occurred at a codon starting with the nucleotide 'a' of an oligonucleotide encoding the dipeptide AR (see FIG. 1). The dipeptide AR is present at 4 positions in the amino acid sequence of SEQ ID NO: 09, i.e. at position 196-197, at position 218-219, at position 242-243, and at position 253-254. As outlined above the formation of a by-product due to a 1→2 frameshift was only observed for the AR dipeptide at position 253-254 of SEQ ID NO: 09. This is more surprising as in the region from position 215 to position 219 of SEQ ID NO: 09, which comprises 3 arginine residues within a total of 5 amino acid residues and which comprises also the dipeptide AR, no 1→2 frameshift could be detected.

The individual dipeptides AR in SEQ ID NO: 09 are encoded as shown in the following table.

TABLE

| position of dipeptide AR | encoding nucleic acid sequence |
|---|---|
| 196-197 | gca cgt |
| 218-219 | gca cgt |
| 242-243 | gcg cgt |
| 253-254 | gcg agg |

Thus, it has been found that the oligonucleotide encoding the dipeptide AR which is comprised in a nucleic acid encoding a larger polypeptide should be selected from the oligonucleotides gca cgt (SEQ ID NO: 03), gcg cgt (SEQ ID NO: 04), and gcc cgt (SEQ ID NO: 05). It has been found that the fourth nucleotide in the oligonucleotide encoding the dipeptide AR should not be 'a'.

The following examples, sequence listing and FIGURES are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

| SEQ ID NO: 01 | Oligonucleotide gcg agg. |
| SEQ ID NO: 02 | Oligonucleotide gcg aga. |
| SEQ ID NO: 03 | Oligonucleotide gca cgt. |
| SEQ ID NO: 04 | Oligonucleotide gcg cgt. |
| SEQ ID NO: 05 | Oligonucleotide gcc cgt. |
| SEQ ID NO: 06 | Dipeptide AR. |
| SEQ ID NO: 07 | Human apolipoprotein A-I. |
| SEQ ID NO: 08 | Removed SLKGS polypeptide. |
| SEQ ID NO: 09 | Tetranectin-apolipoprotein A-I fusion polypeptide comprising expression and purification tags. |
| SEQ ID NO: 10 | Tetranectin-apolipoprotein A-I fusion polypeptide (IVN). |
| SEQ ID NO: 11 | Tetranectin-apolipoprotein A-I fusion polypeptide (PIVN) (SEQ ID NO: 57). |
| SEQ ID NO: 12 | Tetranectin-apolipoprotein A-I fusion polypeptide (XPIVN) (SEQ ID NO: 58). |
| SEQ ID NO: 13 | Tetranectin-apolipoprotein A-I fusion polypeptide (APIVN) (SEQ ID NO: 59). |
| SEQ ID NO: 14 | Tetranectin-apolipoprotein A-I fusion polypeptide (XIVN) comprising hexa-histidine-tag (SEQ ID NO: 55). |
| SEQ ID NO: 15 to 52 | Linker polypeptides. |
| SEQ ID NO: 53 | C-terminal amino acid sequence of main by-product. |
| SEQ ID NO: 54 | Interferon fragment. |
| SEQ ID NO: 55 | Hexa-histidine tag. |
| SEQ ID NO: 56 | IgA protease cleavage site. |

DESCRIPTION OF THE FIGURES

FIG. 1 Deletion or skipping of nucleotide a760 in a tetranectin-apolipoprotein fusion polypeptide encoding nucleic acid results in a 1→2 frameshift and termination of the translation process directly at the next codon. FIGURE discloses SEQ ID NOS 61, 60, 63, and 62, respectively, in order of appearance.

MATERIALS AND METHODS

Protein Determination

The protein concentration was determined by determining the optical density (OD) at 280 nm, using the molar extinction coefficient calculated on the basis of the amino acid sequence.

Recombinant DNA Technique:

Standard methods were used to manipulate DNA as described in Sambrook, J., et al., Molecular cloning: A laboratory manual; Cold Spring Harbor Laboratory Press, Cold Spring Harbor, N.Y., 1989. The molecular biological reagents were used according to the manufacturer's instructions.

Example 1

Making and Description of the *E. Coli* Expression Plasmids

The tetranectin-apolipoprotein A-I fusion polypeptide was prepared by recombinant means. The amino acid sequence of the expressed fusion polypeptide in N- to C-terminal direction is as follows:
 the amino acid methionine (M),
 a fragment of an interferon sequence that has the amino acid sequence of CDLPQTHSL (SEQ ID NO: 54),
 a GS linker,
 a hexa-histidine tag that has the amino acid sequence of HHHHHH (SEQ ID NO: 55),
 a GS linker,
 an IgA protease cleavage site that has the amino acid sequence of VVAPPAP (SEQ ID NO: 56), and
 a tetranectin-apolipoprotein A-I that has the amino acid sequence of SEQ ID NO: 10.

The tetranectin-apolipoprotein A-I fusion polypeptide as described above is a precursor polypeptide from which the final tetranectin-apolipoprotein A-I fusion polypeptides was released by enzymatic cleavage in vitro using IgA protease.

The precursor polypeptide encoding fusion gene was assembled with known recombinant methods and techniques by connection of appropriate nucleic acid segments. Nucleic acid sequences made by chemical synthesis were verified by DNA sequencing. The expression plasmid for the production of tetranectin-apolipoprotein A-I fusion polypeptide of SEQ ID NO: 10 encoding a fusion polypeptide of SEQ ID NO: 09 was prepared as follows.

Making of the E. Coli Expression Plasmid:

Plasmid 4980 (4980-pBRori-URA3-LACI-SAC) is an expression plasmid for the expression of core-streptavidin in E. coli. It was generated by ligation of the 3142 bp long EcoRI/CelII-vector fragment derived from plasmid 1966 (1966-pBRori-URA3-LACI-T-repeat; reported in EP-B 1 422 237) with a 435 bp long core-streptavidin encoding EcoRI/CelII-fragment.

The core-streptavidin E. coli expression plasmid comprises the following elements:
  the origin of replication from the vector pBR322 for replication in E. coli (corresponding to by position 2517-3160 according to Sutcliffe, G., et al., Quant. Biol. 43 (1979) 77-90),
  the URA3 gene of Saccharomyces cerevisiae coding for orotidine 5'-phosphate decarboxylase (Rose, M. et al. Gene 29 (1984) 113-124) which allows plasmid selection by complementation of E. coli pyrF mutant strains (uracil auxotrophy),
  the core-streptavidin expression cassette comprising
    the T5 hybrid promoter (T5-PN25/03/04 hybrid promoter according to Bujard, H., et al. Methods. Enzymol. 155 (1987) 416-433 and Stueber, D., et al., Immunol. Methods IV (1990) 121-152) including a synthetic ribosomal binding site according to Stueber, D., et al. (see before),
    the core-streptavidin gene,
    two bacteriophage-derived transcription terminators, the λ-T0 terminator (Schwarz, E., et al., Nature 272 (1978) 410-414) and the fd-terminator (Beck, E. and Zink, B., Gene 1-3 (1981) 35-58),
    the lacI repressor gene from E. coli (Farabaugh, P. J., Nature 274 (1978) 765-769).

The final expression plasmid for the expression of the tetranectin-apolipoprotein A-I precursor polypeptide was prepared by excising the core-streptavidin structural gene from vector 4980 using the singular flanking EcoRI and CelII restriction endonuclease cleavage site and inserting the EcoRII/CelII restriction site flanked nucleic acid encoding the precursor polypeptide into the 3142 bp long EcoRI/CelII-4980 vector fragment.

Example 2

Expression of Tetranectin-Apolipoprotein A-I

For the expression of the fusion protein there was employed an E. coli host/vector system which enables an antibiotic-free plasmid selection by complementation of an E. coli auxotrophy (PyrF) (see EP 0 972 838 and U.S. Pat. No. 6,291,245).

The E. coli K12 strain CSPZ-2 (leuB, proC, trpE, th-1, ΔpyrF) was transformed by electroporation with the expression plasmid p(IFN-His6-IgA-tetranectin-apolipoprotein A-I) ("His6" disclosed as SEQ ID NO: 55). The transformed E. coli cells were first grown at 37° C. on agar plates.

Fermentation Protocol 1:

For pre-fermentation a M9 medium according to Sambrook et al (Molecular Cloning: A laboratory manual. Cold Spring Harbor Laboratory Press; $2^{nd}$ edition (December 1989) supplemented with about 1 g/l L-leucine, about 1 g/l L-proline and about 1 mg/l thiamine-HCl has been used.

For pre-fermentation 300 ml of M9-medium in a 1000 ml Erlenmeyer-flask with baffles was inoculated with 2 ml out of a primary seed bank ampoule. The cultivation was performed on a rotary shaker for 13 hours at 37° C. until an optical density (578 nm) of 1-3 was obtained.

For fermentation a batch medium according to Riesenberg et al. was used (Riesenberg, D., et al., J. Biotechnol. 20 (1991) 17-27): 27.6 g/l glucose*$H_2O$, 13.3 g/l $KH_2PO_4$, 4.0 g/l $(NH_4)_2HPO_4$, 1.7 g/l citrate, 1.2 g/l $MgSO_4$*7 $H_2O$, 60 mg/l iron(III)citrate, 2.5 mg/l $CoCl_2$*6 $H_2O$, 15 mg/l $MnCl_2$*4 $H_2O$, 1.5 mg/l $CuCl_2$*2 $H_2O$, 3 mg/l $H_3BO_3$, 2.5 mg/l $Na_2MoO_4$*2 $H_2O$, 8 mg/l $Zn(CH_3COO)_2$*2 $H_2O$, 8.4 mg/l Titriplex III, 1.3 ml/l Synperonic 10% anti foam agent. The batch medium was supplemented with 5.4 mg/l thiamin-HCl and 1.2 g/l L-leucine and L-proline respectively. The feed 1 solution contained 700 g/l glucose supplemented with 19.7 g/l $MgSO_4$*7 $H_2O$. The alkaline solution for pH regulation was an aqueous 12.5% (w/v) $NH_3$ solution supplemented with 50 g/l L-leucine and 50 g/l L-proline respectively. All components were dissolved in deionized water.

The fermentation was carried out in a 10 l Biostat C DCU3 fermenter (Sartorius, Melsungen, Germany). Starting with 6.4 l sterile fermentation batch medium plus 300 ml inoculum from the pre-fermentation the batch fermentation was performed at 37° C., pH 6.9±0.2, 500 mbar and an aeration rate of 10 l/min. After the initially supplemented glucose was depleted the temperature was shifted to 28° C. and the fermentation entered the fed-batch mode. Here the relative value of dissolved oxygen ($pO_2$) was kept at 50% (DO-stat, see e.g. Shay, L. K., et al., J. Indus. Microbiol. Biotechnol. 2 (1987) 79-85) by adding feed 1 in combination with constantly increasing stirrer speed (550 rpm to 1000 rpm within 10 hours and from 1000 rpm to 1400 rpm within 16 hours) and aeration rate (from 10 l/min to 16 l/min in 10 hours and from 16 l/min to 20 l/min in 5 hours). The supply with additional amino acids resulted from the addition of the alkaline solution, when the pH reached the lower regulation limit (6.70) after approximately 8 hours of cultivation. The expression of recombinant therapeutic protein was induced by the addition of 1 mM IPTG at an optical density of 70.

At the end of fermentation the cytoplasmatic and soluble expressed tetranectin-apolipoprotein A-I is transferred to insoluble protein aggregates, the so called inclusion bodies, with a heat step where the whole culture broth in the fermenter is heated to 50° C. for 1 or 2 hours before harvest (see e.g. EP-B 1 486 571). Thereafter, the content of the fermenter was centrifuged with a flow-through centrifuge (13,000 rpm, 13 l/h) and the harvested biomass was stored at −20° C. until further processing. The synthesized tetranectin-apolipoprotein A-I precursor proteins were found exclusively in the insoluble cell debris fraction in the form of insoluble protein aggregates, so-called inclusion bodies (IBs).

Samples drawn from the fermenter, one prior to induction and the others at dedicated time points after induction of protein expression are analyzed with SDS-Polyacrylamide gel electrophoresis. From every sample the same amount of cells ($OD_{Target}$=5) are resuspended in 5 mL PBS buffer and disrupted via sonication on ice. Then 100 µL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 µL and to each pellet (=insoluble) fraction 400 µl of SDS sample buffer (Laemmli, U. K., Nature 227 (1970) 680-685) are added. Samples are heated for 15 minutes at 95° C. under shaking to solubilize and reduce all proteins in the samples. After cooling to room temperature 5 µL of each sample are transferred to a 4-20% TGX Criterion Stain Free polyacrylamide gel (Bio-Rad). Additionally 5 µl molecular weight standard (Precision Plus Protein Standard, Bio-Rad) and 3 amounts (0.3 µl, 0.6 µl and 0.9 µl) quantification standard with known product protein concentration (0.1 µg/µl) are positioned on the gel.

The electrophoresis was run for 60 Minutes at 200 V and thereafter the gel was transferred the GelDOC EZ Imager (Bio-Rad) and processed for 5 minutes with UV radiation. Gel images were analyzed using Image Lab analysis software (Bio-Rad). With the three standards a linear regression curve was calculated with a coefficient of >0.99 and thereof the concentrations of target protein in the original sample was calculated.

Fermentation Protocol 2:

For pre-fermentation a M9 medium according to Sambrook et al. (Molecular Cloning: A laboratory manual. Cold Spring Harbor Laboratory Press; 2nd edition (December 1989)) supplemented with about 1 g/l L-leucine, about 1 g/l L-proline and about 1 mg/l thiamine-HCl has been used.

For pre-fermentation 300 ml of modified M9-medium in a 1000 ml Erlenmeyer-flask with baffles was inoculated from agar plate or with 1-2 ml out of a primary seed bank ampoule. The cultivation was performed on a rotary shaker for 13 hours at 37° C. until an optical density (578 nm) of 1-3 was obtained.

For fermentation and high yield expression of tetranectin-apolipoprotein A-I the following batch medium and feeds were used:

8.85 g/l glucose, 63.5 g/l yeast extract, 2.2 g/l $NH_4Cl$, 1.94 g/l L-leucine, 2.91 g/l L-proline, 0.74 g/l L-methionine, 17.3 g/l $KH_2PO_4*H_2O$, 2.02 g/l $MgSO_4*7\ H_2O$, 25.8 mg/l thiamin-HCl, 1.0 ml/l Synperonic 10% anti foam agent. The feed 1 solution contained 333 g/l yeast extract and 333 g/l 85%-glycerol supplemented with 1.67 g/l L-methionine and 5 g/l L-leucine and L-proline each. The feed 2 was a solution of 600 g/l L-Proline. The alkaline solution for pH regulation was a 10% (w/v) KOH solution and as acid a 75% glucose solution was used. All components were dissolved in deionized water.

The fermentation was carried out in a 10 l Biostat C DCU3 fermenter (Sartorius, Melsungen, Germany). Starting with 5.15 l sterile fermentation batch medium plus 300 ml inoculum from the pre-fermentation the fed-batch fermentation was performed at 25° C., pH 6.7±0.2, 300 mbar and an aeration rate of 10 l/min. Before the initially supplemented glucose was depleted the culture reached an optical density of 15 (578 nm) and the fermentation entered the fed-batch mode when feed 1 was started with 70 g/h. Monitoring the glucose concentration in the culture the feed 1 was increased to a maximum of 150 g/h while avoiding glucose accumulation and keeping the pH near the upper regulation limit of 6.9. At an optical density of 50 (578 nm) feed 2 was started with a constant feed rate of 10 ml/h. The relative value of dissolved oxygen ($pO_2$) was kept above 50% by increasing stirrer speed (500 rpm to 1500 rpm), aeration rate (from 10 l/min to 20 l/min) and pressure (from 300 mbar to 500 mbar) in parallel. The expression of recombinant therapeutic protein was induced by the addition of 1 mM IPTG at an optical density of 90.

Seven samples drawn from the fermenter, one prior to induction and the others at dedicated time points after induction of protein expression are analyzed with SDS-Polyacrylamide gel electrophoresis. From every sample the same amount of cells ($OD_{Target}$=5) are resuspended in 5 mL PBS buffer and disrupted via sonication on ice. Then 100 µL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 µL and to each pellet (=insoluble) fraction 200 µL of SDS sample buffer (Laemmli, U. K., Nature 227 (1970) 680-685) are added. Samples are heated for 15 minutes at 95° C. under shaking to solubilize and reduce all proteins in the samples. After cooling to room temperature 5 µL of each sample are transferred to a 10% Bis-Tris polyacrylamide gel (Novagen). Additionally 5 µl molecular weight standard (Precision Plus Protein Standard, Bio-Rad) and 3 amounts (0.3 µl, 0.6 µl and 0.9 µl) quantification standard with known product protein concentration (0.1 µg/µl) are positioned on the gel.

The electrophoresis was run for 35 minutes at 200 V and then the gel was stained with Coomassie Brilliant Blue R dye, destained with heated water and transferred to an optical densitometer for digitalization (GS710, Bio-Rad). Gel images were analyzed using Quantity One 1-D analysis software (Bio-Rad). With the three standards a linear regression curve is calculated with a coefficient of >0.98 and thereof the concentrations of target protein in the original sample was calculated.

At the end of fermentation the cytoplasmatic and soluble expressed tetranectin-apolipoprotein A-I is transferred to insoluble protein aggregates, the so called inclusion bodies (IBs), with a heat step where the whole culture broth in the fermenter is heated to 50° C. for 1 or 2 hours before harvest (see e.g. EP-B 1 486 571). After the heat step the synthesized tetranectin-apolipoprotein A-I precursor proteins were found exclusively in the insoluble cell debris fraction in the form of IBs.

The contents of the fermenter are cooled to 4-8° C., centrifuged with a flow-through centrifuge (13,000 rpm, 13 l/h) and the harvested biomass is stored at −20° C. until further processing. The total harvested biomass yield ranged between 39 g/l and 90 g/l dry matter depending on the expressed construct.

Example 3

Preparation of Tetranectin-Apolipoprotein A-I

Inclusion body preparation was carried out by resuspension of harvested bacteria cells in a potassium phosphate buffer solution (0.1 M, supplemented with 1 mM $MgSO_4$, pH 6.5). After the addition of DNAse the cell were disrupted by homogenization at a pressure of 900 bar. A buffer solution comprising 1.5 M NaCl was added to the homogenized cell suspension. After the adjustment of the pH value to 5.0 with 25% (w/v) HCl the final inclusion body slurry was obtained after a further centrifugation step. The slurry was stored at −20° C. in single use, sterile plastic bags until further processing.

11.75 g inclusion bodies were solubilized in 235 ml 6 M guanidinium-chloride, 50 mM Tris, 1 mM DTT, pH 8.0 for 3.5 hours. After centrifugation the solubilisate was loaded onto a NiNTA column (Qiagen) equilibrated in 50 mM Tris, 1 M NaCl, 8 M urea, pH 8.0. Afterwards the column was flushed with 50 mM Tris, 6 M guanidinium-chloride, pH 8.0 followed by alternating washes with 50 mM Tris, 8 M urea, pH 8.0 and 50 mM Tris, 60% isopropanol (5 cycles), the last step being 50 mM Tris, 8 M urea, pH 8.0. Elution was performed with a pH gradient starting at 50 mM Tris, 0.5 M NaCl, 8 M urea, pH 7.0 to 50 mM Tris, 0.5 M NaCl, 8 M urea, pH 3.0. Peak fractions were pooled and dialyzed against 100 mM Tris, 100 mM NaCl, pH 7.8.

Cleavage with IgA protease was performed at RT for 24 h with a ratio of 1:2000 w/w (IgA protease:protein). This solution was dialyzed against 25 mM sodium acetate, 1 mM Tris, pH 4.5. Urea was added to a final concentration of 8 M. This protein solution was loaded onto a SP-Sepharose (GE) equilibrated with buffer 25 mM sodium acetate, 1 mM Tris, 8 M urea, pH 4.5 and eluted with a gradient to 25 mM sodium acetate, 1 mM Tris, 0.3 M NaCl, 8 M urea, pH 4.5. Fractions were pooled according to SDS-PAGE and dialyzed against 50 mM Tris, 250 mM NaCl, pH 7.5.

Example 4

Analytics of Tetranectin-Apolipoprotein A-I Fusion Polypeptides

Pools or fractions from the NiNTA (Qiagen) and the SP-Sepharose™ (GE) purification columns were desalted and analyzed by electrospray ionization mass spectrometry (ESI-MS).

Desalting was performed offline by size exclusion chromatography using a HR5/20 column (0.7×22 cm, Amersham Bioscience) packed in house with Sephadex G25 Superfine material Amersham Bioscience 17-0851-01) and an isocratic elution with 40% acetonitrile, 2% formic acid with a flow of 1 ml/min. The signal was monitored at 280 nm wavelength and the eluting tetranectin-apolipoprotein fusion polypeptide peak was collected manually.

ESI-MS to monitor the presence of the fragment was performed on a Q-Star Elite QTOF mass spectrometer (Applied Biosystems (ABI), Darmstadt, Germany) equipped with a Triversa NanoMate source system (Advion, Ithaka, USA) using a declustering potential of 50 and a focusing potential of 200. 15 scans per 5 seconds were recorded in the m/z range of 700 to 2000. ESI-MS data were analyzed using two software packages, Analyst (Applied Biosystems (ABI), Darmstadt, Germany) and MassAnalyzer (in-house developed software platform). Mass spectra were checked manually for the presence of signals bearing the molecular mass of the protein fragment resulting from the frameshift at the respective AR dipeptide encoding oligonucleotide (delta of −6269 Da compared to the expected molecular mass of the full-length fusion polypeptide).

The invention claimed is:

1. A method for reducing polypeptide by-product formation by 1→2 frameshift in the recombinant production of a human polypeptide comprising the dipeptide AR (SEQ ID NO: 06), characterized in that the method comprises:
   (a) substituting in the human polypeptide-encoding nucleic acid in the dipeptide AR encoding oligonucleotide gcg agg (SEQ ID NO: 01), or gcg aga (SEQ ID NO: 02) to obtain the oligonucleotide gca cgt (SEQ ID NO: 03), or the oligonucleotide gcg cgt (SEQ ID NO: 04), or the oligonucleotide gcc cgt (SEQ ID NO: 05), thereby producing a substituted polypeptide encoding nucleic acid,
   (b) expressing the substituted polypeptide-encoding nucleic acid using an *E. coli* host/vector, and
   (c) recovering the polypeptide from the cells or the cultivation medium of a cultivation of a cell comprising a nucleic acid encoding the polypeptide and thereby producing the polypeptide.

2. The method according to claim 1, characterized in that the polypeptide has an amino acid sequence selected from the group comprising SEQ ID NO: 09, SEQ ID NO:10, SEQ ID NO:11, SEQ ID NO:12, and SEQ ID NO: 14.

3. The method according to claim 2, characterized in that the polypeptide has the amino acid sequence of SEQ ID NO: 09 or SEQ ID NO: 11.

* * * * *